United States Patent [19]

Walker

[11] 4,059,705
[45] Nov. 22, 1977

[54] DERIVATIVES OF SUBSTITUTED N-ALKYL IMIDAZOLES

[75] Inventor: Keith A. M. Walker, Palo Alto, Calif.

[73] Assignee: Syntex (U.S.A.) Inc., Palo Alto, Calif.

[21] Appl. No.: 665,024

[22] Filed: Mar. 8, 1976

Related U.S. Application Data

[63] Continuation-in-part of Ser. No. 599,616, July 28, 1975, abandoned.

[51] Int. Cl.$^2$ .................. A61K 31/415; C07D 233/60
[52] U.S. Cl. ................................. 424/273 R; 548/341
[58] Field of Search .......................... 260/309; 424/273

[56] References Cited

U.S. PATENT DOCUMENTS 3,531,494  9/1970  Adolphi et al. ..................... 260/309
3,551,444  12/1970  Shen et al. ........................... 260/309

OTHER PUBLICATIONS du Vigneaud et al., J. Amer. Chem. Soc., 1948, vol. 70, pp. 1620-1624.
Skvortsova et al., Chem. Abst., 1970, vol. 72, No. 121437t.

Primary Examiner—Natalie Trousof
Attorney, Agent, or Firm—Alan M. Krubiner

[57] ABSTRACT

Compounds of the formula

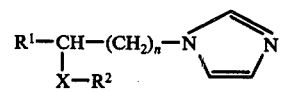

(I)

wherein $R^1$ and $R^2$ are each independently alkyl, cyclohexyl substituted with from one to three lower alkyl groups, or a group of the formula

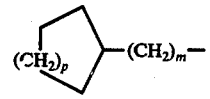

wherein $m$ is an integer of from 0 to 3 and $p$ is an integer of from 1 to 3; X is sulfur or oxygen; $n$ is an integer of from 1 to 8; and the antimicrobial acid addition salts thereof are useful as antifungal, antibacterial and antiprotozoal agents.

33 Claims, No Drawings

DERIVATIVES OF SUBSTITUTED N-ALKYL IMIDAZOLES

RELATED APPLICATIONS

This case is a continuation-in-part of pending U.S. Ser. No. 599,616, filed July 28, 1975, abandoned.

DETAILED DESCRIPTION OF THE INVENTION

The present invention relates to novel chemical compounds which are derivatives of substituted N-alkyl imidazoles. More particularly, the compounds of the present invention are represented by the formula

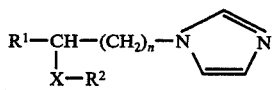

wherein $R^1$ and $R^2$ are each independently alkyl, cyclohexyl substituted with from one to three lower alkyl groups, or a group of the formula

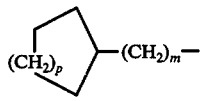

wherein $m$ is an integer of from 0 to 3 and $p$ is an integer of from 1 to 3; X is sulfur or oxygen; $n$ is an integer of from 1 to 8; and the antimicrobial acid addition salts thereof.

In a second aspect the present invention is concerned with a method of combatting fungi, bacteria and protozoa by administering a compound of the present invention or a composition containing same.

As used in the specification and the appended claims, unless specified to the contrary, the following terms have the meaning indicated. The term "alkyl" refers to a straight or branched chain monovalent substituent consisting solely of carbon and hydrogen containing no unsaturation, and having from 1 to 12 carbon atoms. Examples of alkyl groups are methyl, ethyl, n-propyl, i-propyl, n-butyl, t-butyl, pentyl, n-octyl, n-decyl, and n-dodecyl. The term "lower alkyl" refers to the aforementioned groups having from 1 to 4 carbon atoms. "Antimicrobial acid addition salts" of the subject bases refers to those salts which retain the antimicrobial properties of the free bases and which are neither biologically nor otherwise undesirable formed with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

All compounds of formula (I) possess at least one chiral center, i.e., the carbon atom to which are attached the $R^1$, X, $(CH_2)_n$ and H moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compound. Those compounds containing alkyl substituted cyclohexyl rings for $R^1$ or $R^2$ exhibit further isomerism since the alkyl substituents may have either a cis or trans disposition relative to the point of attachment of the cyclohexyl ring and there may be additional chiral centers. All isomers as well as mixtures thereof are intended to be included within the scope of the invention.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of formula (I) with an optically active acid, or by the separation of the diastereomeric salts or esters formed by reaction of racemic compounds of formula (II), infra, with an optically active acid. Exemplary of such optically active acids are the optically active forms of camphor-10-sulfonic acid, α-bromo-camphor-π-sulfonic acid, camphoric acid, menthoxy-acetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of formula (I) or (II).

The subject compounds of formula (I) exhibit antifungal, anti-bacterial and anti-protozoal activity. For example, compounds of the present invention exhibit antifungal activity against human and animal pathogens such as Microsporum audouini,
Mirosporum gypseum,
Microsporum gypseum - canis,
Epidermophyton floccosum
Trichophyton mentagrophytes,
Trichophyton rubrum
Trichophyton tonsurans
Candida albicans, and
Cryptococcus neoformans.

The compounds of the present invention also exhibit anti-fungal activity against the following fungi primarily of agricultural significance Aspergillus flavus,
Cladosporium herbarum,
Fusarium graminearum,
Penicillium notatum, and
Aspergillus niger
Penicillium oxalicum,
Penicillium spinulosum,
Pithomyces chartarum.

In addition, the compounds of the present invention exhibit anti-bacterial activity against human and animal pathogens, such as Staphylococcus aureus,
Streptococcus faecalis,
Corynebacterium acnes,
Erysipelothrix insidiosa,
Escherichia coli,
Proteus vulgaris,
Salmonella choleraesuis,
Pasteurella multocida, and
Pseudomonas aeruginosa.

Moreover, the compounds of the present invention exhibit anti-protozoal activity against protozoa such as Trichomonas vaginalis.

In general, the subject compounds of the instant invention exhibit a low level of toxicity. Moreover, these compounds demonstrate good solubility in the stratum corneum. Since dermatophyte (i.e., parasitic fungal) infections are usually localized in the dead tissue of the stratum corneum, solubility of anti-fungal agents in this tissue significantly enhances their effectiveness.

In view of the aforementioned activities, the subject compounds are found to be useful antimicrobials, having not only pharmaceutical but also agricultural and industrial applications.

Accordingly, a further aspect of the present invention relates to compositions for pharmaceutical, agricultural, and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, poly-alkylene glycols, vaseline and other cream bases; for liquid formulations there may be mentioned, for example, water, oils of vegetable origin and low boiling solvents such as isopropanol, hydrogenated napthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous administration. Intravenous injection of imidazole-type antifungals has been demonstrated to be effective in the treatment of systemic mycoses (see, for example, Drugs, 9, pp. 419–420, 1975, which describes the intravenous administration of miconazole, i.e., 1-[2,4-dichloro-$\beta$-(2',4'-dichlorobenzyloxy)phenethyl]-imidazole nitrate, to patients with systemic candidiasis). Topical application is the preferred method of administration for pharmaceutical applications. For such treatment, an area having an existing fungal, bacterial or protozoal growth, or to be protected against attack by fungi, bacteria or protozoa, may be treated with the subject compounds or compositions by, for example, dusting, sprinkling, spraying, rinsing, brushing, dipping, smearing, coating, impregnating, and the like. Topical pharmaceutical compositions containing the compounds of the present invention exhibit anti-fungal, anti-bacterial and anti-protozoal activity over a wide range of concentration, for example, from about 0.1 to 10.0% by weight of the composition. In any event, the composition to be administered will contain a quantity of the subject compounds in an amount effective for relief or prevention of the specific condition being treated.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g., oral or parenteral) administration it is expedient to administer the active ingredient in amounts between about 1 and 100 mg/kg body weight per day, preferably between about 5 and 50 mg/kg body weight per day, preferably distributed over several applications (e.g., in three individual doses) in order to achieve most effective results. For localized (e.g. topical) administration, however, proportionately less of the active ingredient is required.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known matter. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

The compounds of formula (I) may be considered to consist of two subclasses, those of formulas (Ia) and (Ib) shown below

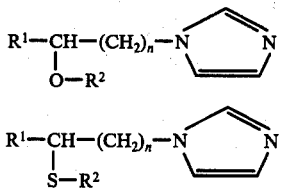

(Ia)

(Ib)

wherein R[1], R[2], and n are as defined above.

Both groups of compounds may be prepared from common intermediates having a free hydroxyl group which is then converted to the ether or thioether, as the case may be, and which may be prepared by a variety of methods, depending upon the length of the $(CH_2)_n$ chain, i.e., the value of n.

A preferred group of compounds within the subgenus (Ia) are those having between 14 and 25 total carbon atoms, particularly between 15 and 23 total carbon atoms. A preferred group of compounds within subgenus (Ib) are those having between 13 and 23 total carbon atoms, particularly between 14 and 21 total carbon atoms.

One particularly preferred group of compounds are those wherein n is 1, R[1] is cyclohexyl or alkyl substituted cyclohexyl, especially wherein the alkyl substitution is in the 2, 4 and/or 6-positions and R[2] is straight chain alkyl. Within this group of compounds particularly preferred compounds are those having mono-alkyl substitution wherein the alkyl group is a 4-t-butyl group or a 2-methyl, ethyl, i-propyl, or t-butyl group. The size of the alkyl chain for R[2] will be dependent upon the nature of the R[1] group so that the total number of carbon atoms in the molecule is as indicated above.

A second particularly preferred group of compounds are those wherein n is 1 or 2 and both R[1] and R[2] are straight chain alkyl groups of from 1 to 12 carbon atoms, with especially preferred compounds having the total number of carbon atoms as indicated above. That is, when n is 1 and X is sulfur, the total number of carbon atoms in R[1] and R[2] is between 8 and 18, preferably between 9 and 16; and when X is oxygen, the total number of carbon atoms in R[1] and R[2] is between 9 and 20, preferably between 10 and 18.

When n is 2, the above ranges are reduced by 1. Thus, the ranges for total carbon atoms in R[1] and R[2] when X is sulfur are between 7 and 18, preferably between 6 and 16; and when X is oxygen are between 8 and 20, preferably between 9 and 18.

As mentioned above, compounds of formula (I) may be prepared by forming an ether or thioether of a suitable alcohol of formula (II)

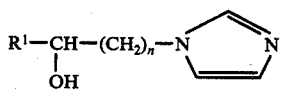

(II)

wherein R[1] and n are as defined above. Compounds of formula (II) may be prepared by a variety of reaction sequences, depending on the size of n.

For example, when n is 1, certain compounds of formula (IIa) may be prepared by reaction scheme A shown below.

REACTION SCHEME A

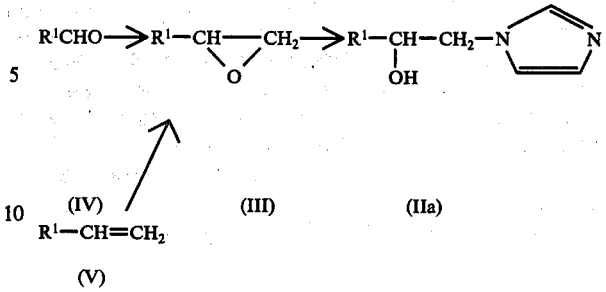

In this reaction scheme the imidazole alcohol of formula (IIa) is formed by opening of a terminal epoxide of formula (III) with imidazole. This reaction is generally carried out using at least one mole and preferably an excess of imidazole relative to epoxide. The reaction may either be carried out in the absence of solvent or, preferably, in an inert organic solvent, for example, a solvent such as dimethylformamide, hexamethylphosphoramide, acetonitrile, and the like. The temperature normally employed for such epoxide opening is in the range of from about −20° to about 100° C. most preferably from about 20° to about 60° C.

Epoxides of formula (III), insofar as they may not be known or readily available, may be prepared by a variety of well known methods, for example epoxidation of a terminal olefin (e.g., (V)) with, for example, a peracid, or by reaction of an aldehyde having one fewer carbon atoms (e.g., (IV)) with the ylide prepared from trimethylsulfoxonium iodide as described, for example, in *J. Am. Chem. Soc.*, 84, p. 867 (1962); ibid, 87, p. 1353 (1965).

When R[1] is a small alkyl group such as methyl, the alcohols of formula (IIa) formed by the opening of the epoxide, or other alcohols of formula (II), described infra, are relatively water soluble. In such cases slight variations in the reaction procedure may be necessary such as for example the use of a low boiling organic solvent such as acetonitrile and either proceeding without the removal of excess imidazole at this stage, by evaporating the solvent and purifying the free base by e.g., chromatography or by acidifying to afford, for example, the hydrochloride salt of the compound of the formula (II), followed by recrystallization of this salt, which can be then cleaved to the free base, if desired.

Another reaction scheme for preparing certain compounds of formula (IIa) is shown in reaction scheme B presented below.

REACTION SCHEME B

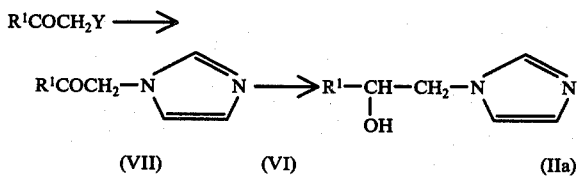

wherein Y is chloro or bromo.

In this reaction scheme the hydroxy compound of formula (IIa) is prepared by reduction of the corresponding ketone (VI) which in turn is prepared by reaction of an α-halo ketone with imidazole.

Certain α-halo ketones are available; others may be readily prepared by methods known in the art, for example, by halogenation of the corresponding methyl ketone, or from terminal acetylenes, acid halides, Grignard reagents or enol ethers.

The α-halo ketone is contacted with imidazole in an inert organic solvent to afford the keto imidazole of formula (VI). The reaction is carried out utilizing at least a molar amount and, preferably, an excess of imidazole relative to halo ketone. The reaction may be carried out in the absence of solvent or, preferably, in an inert organic solvent such as for example dimethylformamide, hexamethylphosphoramide, acetonitrile, and the like. The reaction is suitably carried out at a temperature initially between about −10° and 100° C. most preferably between about 0° and 25° C.

In the next step the keto imidazole of formula (VI) is reduced to the hydroxy imidazole of formula (IIa) utilizing a conventional metal hydride reducing agent such as, for example, sodium borohydride. The reaction is suitably carried out in an alcoholic solvent such as, for example, methanol or ethanol at a reduced temperature, for example, between about −10° and +25° C., most preferably about 0° C.

When $n$ is 2 compounds of formula (IIb) may be prepared according to a variety of synthetic methods. One convenient method for the preparation of certain compounds of formula (IIb) is shown in reaction scheme C presented below.

REACTION SCHEME C

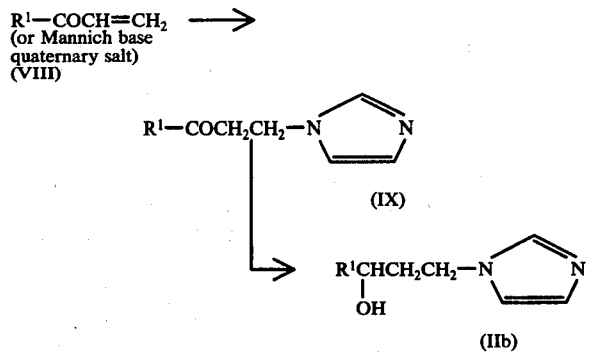

(IIb)

This scheme involves the reaction of imidazole with a vinyl ketone of formula (VIII) (or Mannich base quaternary intermediate) followed by reduction of the resulting keto imidazole of formula (IX) to the hydroxy imidazole of formula (IIb).

Vinyl ketones of formula (VIII), insofar as they may not be known or generally available, may be prepared by a variety of methods well known in the synthetic organic chemistry art, for example, by the addition of vinyl lithium to the corresponding carboxylic acid; by the addition of vinyl lithium to the corresponding aldehyde followed by oxidation of the allylic alcohol thus produced to the vinyl ketone (e.g., *J. Chem Soc.* (C), 1966, p. 1972; *J. Chem. Soc.* (*London*), 1956, p. 3070); or by Mannich reaction of the corresponding methyl ketone, quaternization and elimination.

The first step of the conversion, the reaction of vinyl ketone of formula (VIII) to keto imidazole of formula (IX), is accomplished by contacting the vinyl ketone (or a Mannich quaternary base precursor) with imidazole in an inert organic solvent. The reaction is conveniently carried out utilizing at least a molar amount, and preferably an excess, of imidazole relative to vinyl ketone or Mannich quaternary base in an inert organic solvent, for example, diethyl ether, dichloromethane or dimethylformamide, at a temperature between about 0° and 40° C. preferably about ambient temperature.

The reduction of the keto imidazole of formula (IX) to the hydroxy imidazole of formula (IIb) is carried out in the same manner as described above for the conversion of compound of formula (VI) to that of formula (IIa).

When $n$ is 2 (or greater) certain compounds of formula (II) are conveniently prepared as illustrated in reaction scheme D presented below.

REACTION SCHEME D

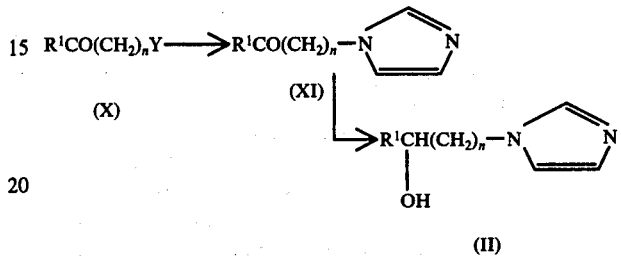

wherein Y is chloro or bromo.

In this reaction scheme an ω-halo (preferably chloro) ketone of the formula (X) is converted to the corresponding keto imidazole of formula (XI) and then to the hydroxy imidazole of the formula (II).

The starting ω-halo ketones, insofar as they may not be known or generally available, may be suitably prepared by for example, the Friedel-Crafts addition of acid halides to ethylene (for $n=2$) and methods described infra.

The conversion from compound (X) to compound (XI) is carried out using imidazole in the same manner as described above for the conversion of (VII) → (VI). When $n$ is 3 or greater, the reaction temperature is between about 0 and 100° C., preferably between 25° and 80° C.

The reduction of the keto imidazole of formula (XI) to the hydroxy imidazole of formula (II) is carried out as previously described for the conversion of (VI) → (IIa).

Certain compounds of formula (IIc) may also be prepared by an alternate procedure depicted in reaction scheme E.

REACTION SCHEME E

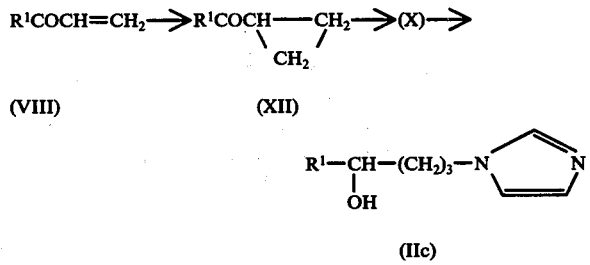

involving the conversion of the previously described vinyl ketone of the formula (VIII) to the corresponding cyclopropyl ketone of the formula (XII), followed by conversion to the γ-halo ketone of formula (X), $n=3$, and then, as described above, to the hydroxy imidazole of formula (IIc).

The cyclopropanation of the vinyl ketone of formula (VIII) may be accomplished by methods known per se, for example as disclosed in *J. Am. Chem. Soc.*, 87, p.

1353 (1965). The resulting cyclopropyl ketone is then opened to afford the γ-halo ketone by treatment with a hydrohalic acid such as, for example, hydrobromic acid.

Certain compounds of formula (II) may also be prepared according to reaction scheme F below.

REACTION SCHEME F

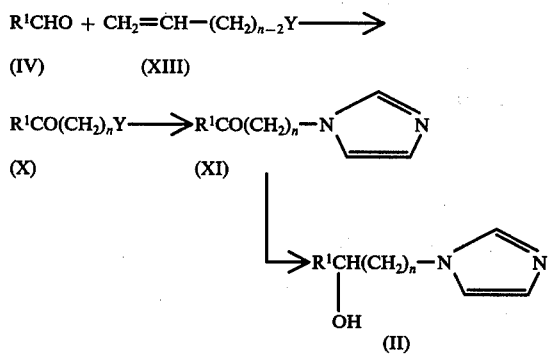

wherein Y is chloro or bromo.

This reaction scheme is particularly useful for preparing compounds wherein n is 4 or greater, but may also be used to prepare compounds where n is 2 or 3. In this scheme, the previously described aldehyde of formula (IV) is reacted with an ω-halo terminal alkene of formula (XIII), readily prepared, for example, by halogenation of the corresponding alcohol, in a free radical addition reaction to afford the previously described halo ketone of formula (X), which is then converted as previously described through the keto imidazole of formula (XI), to the hydroxy imidazole of formula (II). The conversion (IV) + (XIII) → (X) is conveniently carried out using a free radical source such as, for example, diacetyl peroxide, di-tert-butyl peroxide, dibenzoyl peroxide azobisisobutyronitrile; or photochemically, at a temperature between about 50° and 150° C., most preferably between about 60° and 80° C., using an excess of the aldehyde as a solvent medium.

Certain compounds of formula (II) may also be prepared as demonstrated below in reaction scheme G.

REACTION SCHEME G

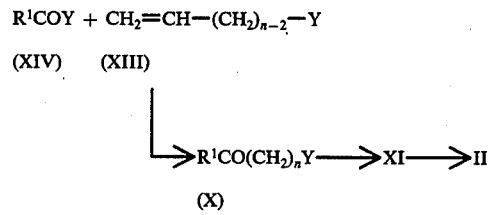

wherein Y is chloro or bromo.

This reaction scheme is conveniently utilized where compounds having n equal to or greater than 4 are desired.

In this reaction scheme an acid halide of formula (XIV), readily prepared from the corresponding carboxylic acid, is reacted with the previously described ω-halo terminal alkene of formula (XIII) to afford the halo ketone of the formula (X), which is then converted, as shown above, to the hydroxy imidazole of formula (II). The addition reaction between compounds of formulas (XIV) and (XIII) is conveniently carried out under conditions as described in G. Olah, "Friedel Crafts and Related Reactions", Vol. 3, Part 2, Interscience Publishers, New York, (1964).

In yet another reaction sequence certain compounds of formula (II) wherein n is 1 or greater may be prepared. This is illustrated below in reaction scheme H.

REACTION SCHEME H

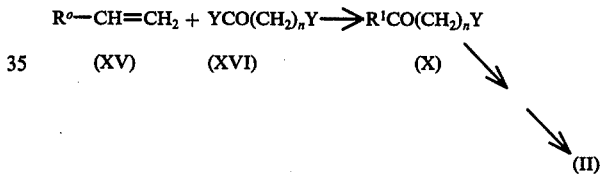

wherein $R^1$ is $R°CH_2CH_2$ and Y is chloro or bromo.

In this scheme the ω-halo ketone of formula (X), described above, is prepared starting with a terminal olefin of formula (XV) and an ω-halo acyl halide of formula (XVI), readily prepared, for example, from the corresponding hydroxyacid. This reaction is carried out under the conditions described above for reaction scheme G.

In reaction scheme I shown below there are illustrated alternative methods for preparing certain compounds of formula (II) wherein n is 1,

REACTION SCHEME I

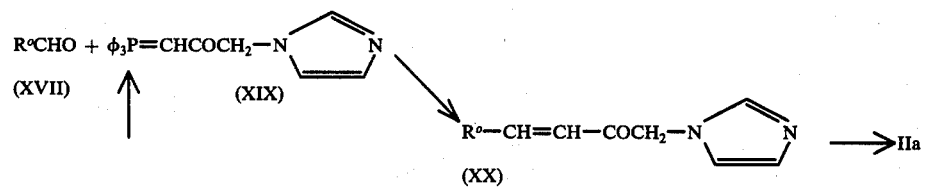

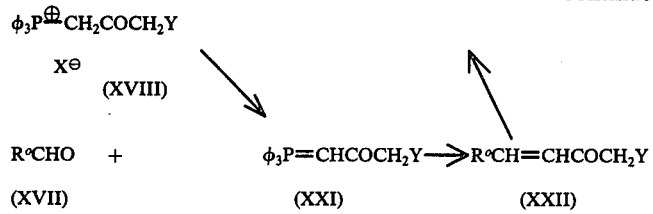

R¹ is R°—CH=CH— or R°CH₂CH₂— and Y is chloro or bromo.

In this scheme an aldehyde of formula (XVII) is reacted, in a Wittig reaction, with an ylide of formula (XIX) or (XXI) to afford the corresponding olefin of formula (XX) or (XXII). The ylide (XXI) is formed, according to methods known per se, from the corresponding phosphonium salt (XVIII), prepared in turn from triphenylphosphine and the corresponding dihalo acetone. To form the ylide of formula (XIX) the phosphonium salt is reacted with an excess of imidazole, in an inert organic solvent such as acetonitrile, dimethylformamide at a temperature between about 25° and 100° C., preferably between about 50° and 80° C., thus affording the imidazole substituted ylide of formula (XIX) which, upon reaction with the aldehyde of formula (XVII) under standard Wittig conditions, (e.g., in acetonitrile at 80° C.) affords the unsaturated keto imidazole of formula (XX).

Alternatively, reaction of the aldehyde of formula (XVII) with the ylide of formula (XXI), prepared in the normal manner from phosphonium salt (XVIII) by treatment with a base such as an alkali metal carbonate, affords the halo unsaturated ketone of formula (XXII). This compound may then be converted to the corresponding imidazole compound of formula (XX) by treatment with imidazole as described for the conversion (VII) → (VI). Reduction of the keto group of compound (XX) affords an unsaturated hydroxy imidazole. The double bond adjacent to the hydroxy moiety may be hydrogenated to afford the compound of formula (IIa). Such hydrogenation may be carried out using standard conditions, for example, using a palladium on charcoal catalyst in a solvent such as methanol or acetone. Alternatively, hydrogenation may be performed prior to reduction of the ketone.

Compounds of formula (II) are converted to the final products of formula (I) wherein X is O by O-alkylation with the appropriate R²Y wherein Y is a leaving group such as halide (chloride, bromide or iodide) or sulfonate ester (e.g., p-toluenesulfonate or methanesulfonate).

The alkylation is carried out by converting the hydroxy group of the compound of formula (II) to its alkali metal salt by treatment with a strong base such as, for example, an alkali metal hydride such as sodium hydride; an alkali metal amide such as sodium amide or potassium amide; and the like. This is preferably done in an inert organic solvent such as, for example, dimethylformamide, hexamethylphosphoramide, tetrahydrofuran, and the like. The alkali metal salt is then contacted with R²Y, preferably in the same solvent system, at a temperature between about 0° and 80° C., most preferably between about 0° and 60° C.

Compounds of formula (I) wherein X is S may be prepared from compounds of formula (II) by a 2-step sequence involving conversion of the hydroxy group to a suitable leaving group such as a halide, (e.g., a chloride or bromide) or a sulfonate ester (e.g., methanesulfonate or p-toluenesulfonate) which is then reacted with a metal salt of the corresponding thiol R²SH.

The conversion from the alcohol to the halide or sulfonate ester is carrier out by means well known in the art. For example, the alcohol may be halogenated using a halogenating agent such as thionyl chloride or thionyl bromide, either neat, or in an inert organic solvent such as dichloromethane or chloroform, at a temperature between about 0° and 80° C., preferably between about 20° and 80° C. The halogenation reaction may be carried out in the presence of a molar equivalent of a base (e.g., pyridine) if desired. Alternate halogenation procedures include, for example, the use of triphenylphosphine with either carbon tetrachloride, carbon tetrabromide, or N-chloro (or N-bromo) succinimide. When utilizing thionyl chloride or thionyl bromide without the use of added base, the hydrochloride or hydrobromide salt of the corresponding halo compound is produced. This salt may be neutralized (e.g., with potassium carbonate) prior to its use in the alkylation step, or the salt may be used directly if excess thiol salt is utilized.

Sulfonate esters may be prepared by the standard procedure of treating the alcohol with an excess of, for example, methanesulfonyl chloride or p-toluenesulfonyl chloride, preferably in the presence of an added base such as pyridine or triethylamine. This reaction is carried out at a temperature from about −20° to +50° C., preferably between about 0° and 20° C.

The above mentioned halide or sulfonate ester is then reacted with a metal salt, preferably an alkali metal salt such as a sodium or potassium salt, of a thiol R²SH. This reaction is carried out in an inert organic solvent such as, for example, tetrahydrofuran, diethylether, methanol, and the like. The salt is formed with a strong base such as for example, sodium hydride or sodium methoxide, at a temperature between about 20° and 80° C.

Compounds of formula (I) wherein n is 1 and X is S may also be prepared as depicted in reaction scheme J below.

REACTION SCHEME J

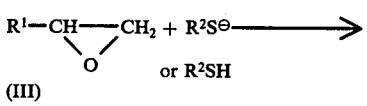

-continued

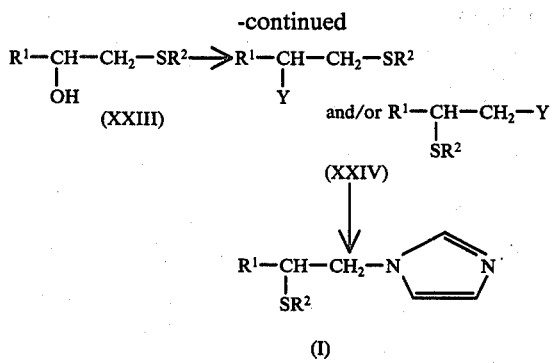

wherein Y is a leaving group.

In this scheme the epoxide of formula (III) described earlier, is opened with a thiol or metal salt thereof, to afford the compound of formula (XXIII). This reaction is carried out utilizing, preferably, an alkali metal salt of the thiol, most preferably the sodium salt, in an inert organic solvent such as, for example, tetrahydrofuran or acetone, at a temperature of between about 0° and 67° C., or using the free thiol in the presence of an acid catalyst, e.g., perchloric acid, under similar conditions.

In the next step the hydroxy group of the compound of formula (XXIII) is converted to a leaving group such as a halide (e.g., chloro or bromo) or sulfonate ester (e.g., p-toluenesulfonate or methanesulfonate) by treatment with e.g., a halogenating agent such as, for example, thionyl chloride, neat, or preferably in an inert solvent such as dichloromethane, or with, for example, p-toluenesulfonyl chloride, in a solvent such as pyridine. The product of formula (XXIV) may exist in either or both forms depicted, and may be interconvertible through an episulfonium intermediate.

In the final step, the compound of formula (XXIV) is converted to the final product of formula (I) by treatment with imidazole. This reaction is carried out in an inert organic solvent such as for example acetonitrile, dimethylformamide, and the like, at a temperature from about 0° to about 80° C.

Alternatively, certain compounds of formula (I) may be formed, in a final step, by hydrogenation of a compound of the formula

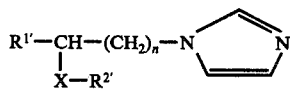

or an acid addition salt thereof wherein $R^{1'}$ and $R^{2'}$ are identical with $R^1$ and $R^2$, respectively, except that $R^{1'}$ and/or $R^{2'}$ contains aliphatic olefinic unsaturation, i.e., wherein $R^{1'}$ and/or $R^{2'}$ is an alkenyl or cycloalkyl alkenyl group. Such hydrogenation may be carried out using conditions well known in the art. For example, the hydrogenation may be carried out at about atmospheric pressure or at higher pressure, and at temperatures from about 0° to about 100° C., in the presence of a suitable supported, unsupported or soluble metal catalyst such as palladium, platinum or tris (triphenylphosphine)chlororhodium, in an inert solvent such as benzene, acetone, methanol, and the like, for a time sufficient to allow the uptake of the required amount of hydrogen.

The subject compounds of the instant invention can be isolated as free bases; however, since many of the compounds in base form are oils, it is more convenient to isolate and characterize the compounds as acid addition salts. These salts are prepared in the usual manner, i.e., by reaction of the base compound with a suitable inorganic or organic acid, described above. Salts formed with dibasic acids (e.g. oxalic acid) may contain one or two molecules of base per molecule of acid. All oxalates described herein contain one molecule of oxalic acid per molecule of imidazole base. If desired, the salts can be readily converted to the free base form by treatment with alkali, such as potassium carbonate, sodium carbonate or sodium or potassium hydroxide.

The following specific examples are illustrative of the present invention and should not be considered as limitative thereof in any manner. In the Examples and the claims, all alkyl moieties, as named, refer to the n-alkyl, unless otherwise specified.

PREPARATION 1

This preparation illustrates the process of reaction scheme A.

A. Propylene oxide (5.8 g.) and imidazole (14 g.) in acetonitrile (100 ml.) were stirred at room temperature for 24 hours and the solvent removed. The water soluble 1-(2-hydroxypropyl)imidazole was purified by preparative thin layer chromatography on silica gel eluting with a solution of 15% methanol in dichloromethane containing 2% ammonium hydroxide solution.

B. To a slurry of 25.5 g. of imidazole in 15 ml. of dry dimethylformamide at 0° C. was added all at once 15.8 g. of 1,2-epoxytetradecane. The mixture was stirred for 4 hours at 0° C. then at 40° C. for three days. After pouring into 500 ml. of water a white precipitate (10 g.) was filtered off and washed with water. The filtrate was extracted 3 times with ethyl acetate and the combined extracts were washed with water, dried and evaporated giving an additional 7.0 g. of material. After recrystallization from ethyl acetate, the product, 1-(2-hydroxytetradecyl)imidazole, had a melting point of 79°–81° C.

Similarly, proceeding as above, utilizing the appropriate epoxide, there may be prepared, for example, the following compounds of formula (IIa):

1-(2-hydroxyoctyl)imidazole
1-(2-hydroxydecyl)imidazole
1-(2-hydroxydodecyl)imidazole
1-(2-hydroxy-2-cyclohexylethyl)imidazole
1-(2-hydroxy-3-cyclohexylpropyl)imidazole
1-(2-hydroxy-4-cyclohexylbutyl)imidazole
and
1-(2-hydroxy-5-cyclohexylpentyl)imidazole.

PREPARATION 2

This preparation illustrates the process of reaction scheme B.

A. Chloroacetone (9.25 g.) in dry acetonitrile was added dropwise with stirring and ice cooling to a slurry of imidazole (13.6 g.) in acetonitrile (100 ml.). The mixture was stirred for 4 hours with ice cooling and then for 24 hours at room temperature. The solvent was removed and the product isolated by chromatography on silica gel, eluting with 10% methanol/dichloromethane. This material in 100 ml. of methanol was treated with excess sodium borohydride at 0° C. for 1 hour and acidified with methanolic hydrogen chloride. The solvent was removed, ethyl acetate added and the stirred mixture treated dropwise with saturated potassium carbonate solution until basic. The ethyl acetate was then decanted, dried, evaporated and the residue chromatographed on silica gel eluting with 10% methanol/dichloromethane to give pure 1-(2-hydroxypropyl)imidazole.

B. To a stirred cold (0° C.) mixture of 21.9 g. of anhydrous cuprous iodide in 700 ml. of anhydrous ether was added under nitrogen 95.2 ml. of 2.1 M methyl lithium (c.f. *J. Org. Chem,* 33, p.949 (1968)). Some yellow precipitate formed immediately. To the above mixture was added rapidly with stirring 6.21 g. of 1-acetyl-1-cyclohexene. The mixture became yellow and was stirred for an additional ½ hour at 0° C. The reaction mixture was then poured into 400 ml. of saturated ammonium chloride solution, stirred and filtered. The colorless ether layer was separated and the blue aqueous layer was extracted 3 times with ether. The combined ether portions were dried over magnesium sulfate and concentrated to afford 6.5 g. of 2-methyl-1-acetylcyclohexane as a yellow oil.

This material was brominated following the procedure in Tetrahedron, 26, p. 5611 (1970), as follows:

To 2.80 g. of the above material in 25 ml. of anhydrous methanol was added all at once 3.20 g. of bromine in 25 ml. of anhydrous methanol at 0° C. and the mixture stirred until the bromine color disappeared (approximately 30 minutes). The solvent was removed, ether added and the ethereal solution washed with saturated sodium bicarbonate solution, dried over magnesium sulfate and evaporated to afford 4.1 g. of 2-methyl-1-bromoacetylcyclohexane, as a brown oil.

A mixture of 3.85 g. of the above bromo compound, 5.96 g. of imidazole and 15 ml. of dry dimethylformamide was stirred at 0° C. for 6 hours, then overnight at room temperature. The resulting yellow solution was poured into 300 ml. of saturated sodium chloride solution and extracted with ethyl acetate. The ethyl acetate extract was dried and evaporated and the resulting oil dissolved in ether. After treatment with oxalic acid, there was obtained 1-[2-(2-methylcyclohexyl)-2-oxoethyl]imidazole oxalate, recrystallized from absolute ethanol as colorless blades, m.p. 155.5°-166° C. (dec.).

The above oxalate salt in 200 ml. of absolute methanol was treated with excess sodium borohydride at 0° C. and stirred for 1 hour. After removal of the solvent, a small quantity of water was added to the residue and the product extracted with ethyl acetate. The combined extract was dried over magnesium sulfate and evaporated. The resulting 1-[2-(2-methylcyclohexyl)-2-hydroxyethyl]imidazole was recrystallized from ethyl acetate to afford a white solid, m.p. 150°-154° C.

If desired prior to the sodium borohydride reduction, the ketone may be equilibrated with methanolic potassium hydroxide under nitrogen to assure complete conversion to the trans-isomer.

C. To a stirred solution of 18.03 g. of 2-t-butyl-1-acetylcyclohex-1-(and-5-)ene (prepared from 2-t-butylcyclohexanone by a method analagous to that described in Ann. Chim., 1968, p. 543) in 1 liter of ether containing a small amount of gaseous hydrogen chloride was added 41 g. of 2,4,4,6-tetrabromocyclohexa-2,5-dienone (ref. *J. Chem. Soc. (C),* 1971, p. 3652). The resulting yellow solution was stirred in the dark at room temperature overnight during which time it became colorless. The colorless solution was washed with dilute aqueous sodium carbonate solution, dried over magnesium sulfate and evaporated. The resulting oil, containing 2-t-butyl-1-bromoacetylcyclohex-1-(and -5-)ene, was used directly in the next step.

A solution of 7.8 g. of the crude bromide from the previous step, 11 g. of imidazole and 15 ml. of dry dimethylformamide was stirred at 0° for 4 hours and overnight at room temperature. The resulting yellow solution was poured into 150 ml. of water and extracted with benzene. The combined benzene extracts were washed with water, dried over magnesium sulfate and concentrated to afford a yellow oil. Chromatography on silica gel eluting with 10% methanol/dichloromethane afforded 1-[2-(2-t-butylcyclohex-1-(and -5-) enyl)-2-oxoethyl]imidazole which was converted to its oxalate salt.

To a 0° C. solution of 3.0 g of the above material in 100 ml. of anhydrous methanol was added an excess of sodium borohydride and the mixture was stirred for 1 hour. After removal of the solvent and addition of water the residue was extracted with ethyl acetate. The combined ethyl acetate extracts were dried over magnesium sulfate and evaporated. The crude alcohol was chromatographed on silica gel, eluting with 10% methanol/dichloromethane to afford pure 1-[2-(2-tert-butylcyclohex-1-(and -5-)enyl)-2-hydroxyethyl]imidazole.

A solution of 3.0 g. of the above material (free base) in 80 ml. of methanol was catalytically hydrogenated over 5% palladium on charcoal at room temperature and atmospheric pressure. After complete uptake of hydrogen the catalyst was filtered off and the filtrate evaporated to afford the product, cis-1-[2-(2-tert-butylcyclohexyl)-2-hydroxyethyl]imidazole.

The trans isomer may be prepared by first hydrogenating the imidazolyl ketone over palladium/charcoal catalyst in acetone, equilibrating with potassium hydroxide in methanol under nitrogen, and reducing with sodium borohydride in methanol.

Similarly, proceeding as above, utilizing the appropriate haloketone, there may be prepared, for example, the compounds of formula (IIa) listed in preparation 1, as well as the following compounds:
1-[2-hydroxy-2-(4-tert-butylcyclohexyl)ethyl]imidazole
1-(2-hydroxy-4-cyclohexylbutyl)imidiazole
1-(2-hydroxy-5-cyclohexylpentyl)imidiazole

PREPARATION 3

This preparation illustrates the process of reaction scheme C.

Oct-1-en-3-ol (5.0 g.) in ether (100 ml.) was treated dropwise at ambient temperature with Jones reagent (20 ml.). After 30 minutes the mixture was separated, the aqueous phase extracted with ether, the combined ether solutions washed with saturated sodium bicarbonate solution, and water, and dried over magnesium sulfate. This solution was treated with imidazole (6 g.) with stirring at room temperature for 36 hours, washed to remove excess imidazole, dried over magnesium sulfate and evaporated to give 1-(octan-3-onyl)-imidazole as an amber oil (6.5 g.). The hydrochloride was recrystallized from acetone as colorless flakes, m.p. 104-106° C.

The above free base (6.0 g.) in methanol (100 ml.) was reduced with excess sodium borohydride with stirring and ice cooling. After 1 hour the solvent was removed, 400 ml. of ether was added followed by 5 ml. of sodium chloride solution and 5 ml. of water and the mixture stirred until the organic layer was clear. The ether solution was separated, dried over magnesium sulfate and evaporated to give 1-(3-hydroxyoctyl)imidazole as a mobile almost colorless oil.

Similarly, proceeding as above, utilizing the appropriate vinyl ketone, there may be prepared for example, the following compounds of formula (IIb):
1-(3-hydroxy-3-cyclohexylpropyl)imidazole
1-(3-hydroxybutyl)imidazole
1-[3-hydroxy-3-(2-methylcyclohexyl)propyl]-imidazole
1-[3-hydroxy-3-(2-tert-butylcyclohexyl)propyl]-imidazole
1-[3-hydroxy-3-(4-tert-butylcyclohexyl)propyl]-imidazole
1-(3-hydroxy-4-cyclohexylbutyl)imidazole
1-(3-hydroxy-5-cyclohexylpentyl)imidazole
1-(3-hydroxy-6-cyclohexylhexyl)imidazole
1-(3-hydroxynonyl)imidazole
1-(3-hydroxydecyl)imidazole
1-(3-hydroxyundecyl)imidazole
1-(3-hydroxydodecyl)imidazole
1-(3-hydroxytetradecyl)imidazole
1-(3-hydroxyheptyl)imidazole

PREPARATION 4

This preparation illustrates the process of reaction scheme D.

A. Cyclohexyl (2-chloroethyl)ketone (3.2 g.) and imidazole (7.0 g.) in dimethylformamide (5 ml.) were stirred at 25° C. for 24 hours and poured into 50 ml. water. The product, 1-(3-cyclohexylpropan-3-onyl)imidazole, was extracted with ether, the extracts washed with water, dried and evaporated and the residue used in the next step. The oxalate salt, recrystallized from ethyl acetate, had m.p. 135°–135.5° C.

The above material (2.95 g.) in 80 ml. of methanol was treated at 0° C. with excess sodium borohydride. When the reaction was complete, the solvent was evaporated, 50 ml. of water was added and the product was extracted with ether. The extracts were washed with water, dried and evaporated to give 1-(3-hydroxy-3-cyclohexylpropyl)imidazole as a colorless gum.

B. 5-Bromo-2-pentanone (1.65 g.) and imidazole (3.5 g.) in 15 ml. acetonitrile were stirred at 60° C. for 48 hours and the solvent removed. The residue was chromatographed on silica gel, eluting with 10% methanol in dichloromethane to give 1-(n-pentan-4-onyl)imidazole. This material in 40 ml. methanol was reduced with sodium borohydride in a similar manner to that described in Preparation 2A to give 1-(4-hydroxy-n-pentyl)imidazole.

Similarly, proceeding as above, utilizing the appropriate haloketone, there may be prepared, for example, those compounds of formula (IIb) listed in Preparation 3, as well as:
1-(4-hydroxyoctyl)imidazole
1-(4-hydroxy-4-cyclohexylbutyl)imidazole
1-[4-hydroxy-(2-methylcyclohexyl)butyl]imidazole
1-[4-hydroxy-(2-tert-butylcyclohexyl)butyl]-imidazole
1-[4-hydroxy-(4-tert-butylcyclohexyl)butyl]-imidazole
1-(4-hydroxy-5-cyclohexylpentyl)imidazole
1-(4-hydroxy-6-cyclohexylhexyl)imidazole
1-(4-hydroxy-hexadecyl)imidazole
1-(4-hydroxytridecyl)imidazole
1-(6-hydroxyheptyl)imidazole
1-(6-hydroxydodecyl)imidazole
1-(6-hydroxy-6-cyclohexylhexyl)imidazole
1-(6-hydroxyoctadecyl)imidazole
1-(9-hydroxydecyl)imidazole
1-(9-hydroxytetradecyl)imidazole
1-(9-hydroxy-9-cyclohexylnonyl)imidazole
1-(9-hydroxy-11-cyclohexylundecyl)imidazole
and
1-(9-hydroxyoctadecyl)imidazole

PREPARATION 5

This preparation illustrates the process of reaction scheme I.

Chloroacetylmethyltriphenylphosphonium chloride (7.3 g.) and imidazole (7.3 g.) in acetonitrile (60 ml.) were stirred and heated at 80° C. for 2 days. The resulting solution was evaporated and the residue treated with water, extracted with benzene and the benzene extracts washed with water, dried over magnesium sulfate and evaporated. Recrystallization from ethyl acetate/cyclohexane afforded the product, 1-imidazolylacetylmethylenetriphenylphosphorane, as colorless blades, m.p. 154.5°–158° C.

Valeraldehyde (2.4 g.) and the above phosphorane (3.85 g.) in acetonitrile (30 ml.) was stirred and refluxed overnight and then evaporated to dryness. The residue was chromatographed on silica gel, eluting with acetone/dichloromethane to afford pure 1-(oct-3-en-2-onyl)imidazole.

This material was reduced with excess sodium borohydride as described in preparation 2, to afford 1-(2-hydroxyoct-3-enyl)imidazole.

2.5 G. of this material in 30 ml. of methanol was hydrogenated at ambient temperature and pressure over a 10% palladium on charcoal catalyst. When the uptake of hydrogen ceased, the solution was filtered, and the solvent removed to afford 1-(2-hydroxyoctyl)imidazole as an oil. If desired, the hydrochloride salt may be precipitated from ether as a white solid.

Similarly, proceeding as above, utilizing the appropriate aldehyde, there may be prepared, for example, the following compounds of formula (Ia):
1-(2-hydroxy-4-cyclohexylbutyl)imidazole
1-(2-hydroxy-5-cyclohexylpentyl)imidazole
and
1-(2-hydroxytetradecyl)imidazole.

EXAMPLE 1

A. A mixture of 380 mg. of 1-(3-hydroxy-3-cyclohexylpropyl)imidazole and 90 mg. of sodium hydride (56% dispersion in mineral oil) in 3 ml. of dry hexamethylphosphoramide was stirred under nitrogen at room temperature for one hour and at 45° C. for one hour. After the evolution of hydrogen ceased, the solution was cooled in an ice bath and a solution of 440 mg. of n-decylbromide in 1 ml. hexamethylphosphoramide added dropwise keeping the temperature below 10° C. The solution was stirred for one hour at room temperature, 2 hours at 45° C. and let stand overnight. The resulting mixture was then poured into water, extracted with ether, the ether extracts washed with water, dried and evaporated. The oily product was chromatographed in silica gel, eluting with 20% acetone/dichloromethane to give pure 1-(3-decycloxy-3-cyclohexylpropyl)imidazole, as a colorless gum, which was converted to its oxalate salt by treatment of an ethereal solution with oxalic acid in ether, which salt slowly crystallized from the ethereal solution as colorless rods, m.p. 81°–84° C.

EXAMPLE 2

A solution of 1.5 g of 1-(3-hydroxyoctyl)imidazole was treated with 5 ml. of thionyl chloride and the solution stirred at room temperature for one hour. Evaporation to dryness afforded 1-(3-chlorooctyl)imidazole hydrochloride.

The free base may be obtained for use in the subsequent alkylation steps, if desired, by shaking the hydrochloride in dichloromethane with excess aqueous potassium carbonate solution, washing the organic layer with water, drying over magnesium sulfate and evaporating to dryness.

EXAMPLE 3

500 Mg. of 1-(3-chlorooctyl)imidazole in 10 ml. tetrahydrofuran was added to a fully reacted mixture of 750 mg. of n-octylmercaptan and 200 mg. of 56% sodium hydride dispersion in mineral oil in 30 ml. of tetrahydrofuran. After stirring under reflux for 12 hours the solvent was evaporated under vacuum and 150 ml. of ether was added. The resulting mixture was washed twice with water and the ethereal solution dried and evaporated. The residue was chromatographed on silica gel, eluting with 20% acetone/dichloromethane to afford 1-(3-octylthiooctyl)imidazole, as an oil. This material was converted to the oxalate salt by treatment of an ethereal solution with oxalic acid in ether until precipitation was complete, which salt was recrystallized from ethyl acetate as snow-white microcrystals, m.p. 105°–108° C.

EXAMPLE 4

Propylene oxide (2.9 g.) in dry tetrahydrofuran (10 ml.) was added all at once to a stirred suspension obtained by adding 240 mg. of 56% sodium hydride dispersion in mineral oil to 12 g. of dodecylmercaptan in 200 ml. of dry tetrahydrofuran.

After stirring overnight at 60° C. the solvent was removed, the residue treated with water and extracted with ether. The ether extract was washed, dried and evaporated to afford a colorless oil.

The above oil was treated with 50 ml. of thionyl chloride at room temperature for 60 minutes, and the solution evaporated to dryness. The residue was treated with 18 g. of imidazole and 100 ml. of acetonitrile and stirred overnight at room temperature and at 60° C. for 4 hours. The solvent was evaporated and after the addition of 80 ml. of water the residue was extracted with ether. The ether extract was washed with water, dried and evaporated to afford 1-(2-dodecylthiopropyl)imidazole as an oil, which was purified by chromatography on silica gel eluting with 10% methanol in dichloromethane. The nitrate salt was precipitated by addition of 70% nitric acid to a solution of the product in ether. Recrystallization from ethyl acetate gave snow-white microcrystals, m.p. 79.5°–81° C.

EXAMPLE 5

Following the procedures in Preparations 1, 2, or 5 and Examples 1; 2,3; or 4, using equivalent amounts of the appropriate starting materials, there may be obtained the following compounds. Where indicated, the compounds may be further characterized by conversion to the indicated acid addition salt.

1-(2-dodecyloxypropyl)imidazole
1-(2-heptylthiooctyl)imidazole
1-(2-octylthiooctyl)imidazole- oxalate salt, m.p. 80°–95° C.
1-(2-nonylthiooctyl)imidazole
1-(2-nonyloxyoctyl)imidazole
1-(2-decyloxyoctyl)imidazole
1-(2-hexylthiodecyl)imidazole
1-(2-octyloxydecyl)imidazole
1-(2-butylthiododecyl)imidazole
1-(2-hexyloxydodecyl)imidazole 1-(2-ethylthiotetradecyl)imidazole- oxalate salt, m.p. 95°–97° C.
1-(2-butoxytetradecyl)imidazole
1-[2-(4-tert-butylcyclohexyloxy)propyl]imidazole
1-(2-decylthiooctyl)imidazole
1-(2-octyloxyoctyl)imidazole
1-[2-(4-methylcyclohexylthio)octyl]imidazole
1-(2-cyclohexylethoxyoctyl)imidazole
1-(2-decyloxy-2-cyclohexylethyl)imidazole
1-(2-decylthio-2-cyclohexylethyl)imidazole
1-[2-octylthio-2-(2-methylcyclohexyl)ethyl]-imidazole
1-[2-hexyloxy-2-(2-methylcyclohexyl)ethyl]-imidazole
1-[2-pentylthio-2-(2-tert-butylcyclohexyl)ethyl]-imidazole
1-[2-propoxy-2-(2-tert-butylcyclohexyl)ethyl]-imidazole
1-[2-pentylthio-2-(4-tert-butylcyclohexyl)ethyl]-imidazole
1-[2-propoxy-2-(4-tert-butylcyclohexyl)ethyl]-imidazole
1-(2-nonylthio-3-cyclohexylpropyl)imidazole
1-(2-hexyloxy-4-cyclohexylbutyl)imidazole
1-(2-heptylthio-5-cyclohexylpentyl)imidazole
1-(2-methylthiotetradecyl)imidazole
1-(2-ethoxytetradecyl)imidazole
1-(2-decylthio-1-cyclopentylethyl)imidazole
1-(2-decylthio-2-cycloheptylethyl)imidazole
1-(2-propylthiooctyl)imidazole
1-(2-butylthiooctyl)imidazole
1-(2-pentylthiooctyl)imidazole
1-(2-hexylthiooctyl)imidazole
1-(2-butyloxyoctyl)imidazole
1-(2-pentyloxyoctyl)imidazole
1-(2-hexyloxyoctyl)imidazole
1-(2-heptyloxyoctyl)imidazole
1-(2-methylthiodecyl)imidazole
1-(2-ethylthiodecyl)imidazole
1-(2-propylthiodecyl)imidazole
1-(2-butylthiodecyl)imidazole
1-(2-ethoxydecyl)imidazole
1-(2-propoxydecyl)imidazole
1-(2-butoxydecyl)imidazole
1-(2-pentyloxydecyl)imidazole

EXAMPLE 6

Following the procedures in Preparations 3 or 4 and Examples 1 or 2 and 3, using equivalent amounts of the appropriate starting materials, there may be obtained the following compounds. Where indicated, the compounds may be further characterized by conversion to the indicated acid addition salt.

1-(3-dodecyloxybutyl)imidazole
1-(3-dodecylthiobutyl)imidazole- oxalate salt, m.p. 85.5°–89° C. (dec.)
1-[3-(4-tert-butylcyclohexyloxy)butyl]imidazole
1-(3-nonylthiooctyl)imidazole
1-(3-heptylthiooctyl)imidazole
1-(3-decyloxyoctyl)imidazole 1-(3-heptylthiononyl)imidazole
1-(3-decyloxynonyl)imidazole
1-(3-hexylthiodecyl)imidazole
1-(3-octyloxydecyl)imidazole
1-(3-pentylthioundecyl)imidazole
1-(3-heptyloxyundecyl)imidazole
1-(3-butylthiododecyl)imidazole
1-(3-hexyloxydodecyl)imidazole
1-[3-(4-methylcyclohexylthio)octyl]imidazole
1-(3-cyclohexylmethoxyoctyl)imidazole
1-(3-nonyloxy-3-cyclohexylpropyl)imidazole
1-(3-decylthio-3-cyclohexylpropyl)imidazole
1-[3-octylthio-3-(2-methylcyclohexyl)propyl]-imidazole
1-[3-hexyloxy-3-(2-methylcyclohexyl)propyl]-imidazole
1-[3-pentylthio-3-(2-tert-butylcyclohexyl)propyl]-imidazole
1-[3-propoxy-3-(2-tert-butylcyclohexyl)propyl]-imidazole
1-[3-pentylthio-3-(4-tert-butylcyclohexyl)propyl]-imidazole
1-[3-propoxy-3-(4-tert-butylcyclohexyl)propyl]-imidazole
1-(3-octylthio-4-cyclohexylbutyl)imidazole
1-(3-pentyloxy-5-cyclohexylpentyl)imidazole
1-(3-hexylthio-6-cyclohexylhexyl)imidazole
1-(3-ethylthiotetradecyl)imidazole
1-(3-butoxytetradecyl)imidazole
1-(3-cyclohexylmethoxytetradecyl)imidazole
1-(3-methylthiotetradecyl)imidazole
1-(3-butylthiooctyl)imidazole
1-(3-pentylthiooctyl)imidazole
1-(3-hexylthiooctyl)imidazole
1-(3-pentyloxyoctyl)imidazole
1-(3-hexyloxyoctyl)imidazole
1-(3-heptyloxyoctyl)imidazole
1-(3-octyloxyoctyl)imidazole
1-(3-pentylthioheptyl)imidazole
1-(3-hexylthioheptyl)imidazole
1-(3-hepthylthioheptyl)imidazole
1-(3-hexyloxyheptyl)imidazole
1-(3-heptyloxyheptyl)imidazole
1-(3-octyloxyheptyl)imidazole
1-(3-nonyloxyheptyl)imidazole

EXAMPLE 7

Following the procedures in Preparation 4 and Examples 1 or 2 and 3, using equivalent amounts of the appropriate starting materials, there may be obtained the following compounds. Where indicated, the compounds may be further characterized by conversion to the indicated acid addition salt.

1-(4-dodecyloxypentyl)imidazole
1-(4-dodecylthiopentyl)imidazole
1-[4-(4-tertbutylcyclohexyloxy)pentyl]imidazole
1-(4-nonylthiooctyl)imidazole
1-(4-heptyloxyoctyl)imidazole
1-[4-(4-methylcyclohexylthio)octyl]imidazole
1-(4-cyclohexylethoxyoctyl)imidazole
1-(4-octyloxy-4-cyclohexylbutyl)imidazole
1-(4-nonylthio-4-cyclohexylbutyl)imidazole
1-[4-heptylthio-4-(2-methylcyclohexyl)butyl]-imidazole
1-[4-pentyloxy-4-(2-methylcyclohexyl)butyl]-imidazole
1-[4-butylthio-4-(2-tert-butylcyclohexyl)butyl]-imidazole
1-[4-ethoxy-4-(2-tert-butylcyclohexyl)butyl]-imidazole
1-[4-butylthio-4-(4-tert-butylcyclohexyl)butyl]-imidazole
1-[4-ethoxy-4-(4-tert-butylcyclohexyl)butyl]-imidazole
1-(4-heptylthio-5-cyclohexylpentyl)imidazole
1-(4-pentyloxy-6-cyclohexylhexyl)imidazole
1-(4-methylthiohexadecyl)imidazole
1-(4-cyclohexylmethylthiotridecyl)imidazole
1-(6-decylthioheptyl)imidazole
1-[6-(2-methylcyclohexyloxy)heptyl]imidazole
1-(6-butylthiododecyl)imidazole
1-(6-cyclohexylthiododecyl)imidazole
1-(6-hexylthio-6-cyclohexylhexyl)imidazole
1-(6-butoxy-6-cyclohexylhexyl)imidazole
1-(6-methylthiooctadecyl)imidazole
1-(9-decylthiodecyl)imidazole
1-(9-hexyloxydecyl)imidazole
1-(9-ethylthiotetradecyl)imidazole
1-(9-butylthio-9-cyclohexylnonyl)imidazole
1-(9-ethylthio-11-cyclohexylundecyl)imidazole and
1-(9-methylthio-octadecyl)imidazole

EXAMPLE 8

A solution of oxalic acid in ether was added dropwise to a stirred solution of 2.0 g. of 1-(3-octylthiooctyl)imidazole in 30 ml. of anhydrous ether until precipitation was complete. The product was filtered off, washed with ether, air dried, and recrystallized from ethyl acetate to yield 1-(3-octylthiooctyl)imidazole oxalate, m.p. 105°–108° C.

In similar manner, all compounds of Formula (I) in base form can be converted to their antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic or salicylic acid.

EXAMPLE 9

1-(3-Octylthiooctyl)imidazole oxalate (2.0 g.) in 100 ml. of dichloromethane was shaken with excess dilute potassium carbonate solution until the salt was completely dissolved. The organic layer was then separated, washed twice with water, dried over magnesium sulfate and evaporated to yield 1-(3-octylthiooctyl)imidazole as an oil.

In similar manner, the antimicrobial acid addition salts of all compounds of Formula (I) can be converted to the corresponding compounds in base form.

EXAMPLE 10

The following illustrates the preparation of representative pharmaceutical formulations which may be used for controlling fungi, bacteria and protozoa, utilizing an active compound such as a salt of 1-(3-octylthiooctyl)imidazole.

| A. Topical Formulation | grams |
|---|---|
| Active compound | 0.2 – 2 |
| Span 60 | 2 |
| Tween 60 | 2 |
| Mineral oil | 5 |

-continued

| A. Topical Formulation | | grams |
|---|---|---|
| Petrolatum | | 10 |
| Methyl paraben | | 0.15 |
| Propyl paraben | | 0.05 |
| BHA (butylated hydroxy anisole) | | 0.01 |
| Water | qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

| B. I.V. Formulation | |
|---|---|
| Active compound | 0.5 g. |
| Propylene glycol | 20 g. |
| Polyethylene glycol 400 | 20 g. |
| Tween 80 | 1 g. |
| 0.9 Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

| C. Oral Formulation | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

I claim as my invention:

1. A compound of the formula

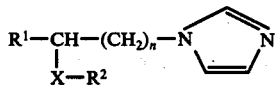

(I)

wherein X is sulfur, n is 1 or 2, and $R^1$ and $R^2$ are each independently straight chain alkyl of from 1 to 12 carbon atoms such that the total number of carbon atoms in $R^1$ and $R^2$ is between 7 and 18; and the antimicrobial acid addition salts thereof.

2. The compound of claim 1 which is 1-(2-heptylthiooctyl)imidazole and the antimicrobial acid addition salts thereof.

3. The compound of claim 1 which is 1-(2-octylthiooctyl)imidazole and the antimicrobial acid addition salts thereof.

4. The compound of claim 1 which is 1-(2-nonylthiooctyl)imidazole and the antimicrobial acid addition salts thereof.

5. The compound of claim 1 which is 1-(2-hexylthiodecyl)imidazole and the antimicrobial acid addition salts thereof.

6. The compound of claim 1 which is 1-(2-butylthiododecyl)imidazole and the antimicrobial acid addition salts thereof.

7. The compound of claim 1 which is 1-(2-ethylthiotetradecyl)imidazole and the antimicrobial acid addition salts thereof.

8. The compound of claim 1 which is 1-(3-octylthiooctyl)imidazole and the antimicrobial acid addition salts thereof.

9. The compound of claim 1 which is 1-(3-heptylthiooctyl)imidazole and the antimicrobial acid addition salts thereof.

10. The compound of claim 1 which is 1-(3-nonylthiooctyl)imidazole and the antimicrobial acid addition salts thereof.

11. The compound of claim 1 which is 1-(3-heptylthiononyl)imidazole and the antimicrobial acid addition salts thereof.

12. The compound of claim 1 which is 1-(3-hexylthiodecyl)imidazole and the antimicrobial acid addition salts thereof.

13. The compound of claim 1 which is 1-(3-pentylthioundecyl)imidazole and the antimicrobial acid addition salts thereof.

14. The compound of claim 1 which is 1-(3-butylthiododecyl)imidazole and the antimicrobial acid addition salts thereof.

15. The compound of claim 1 which is 1-(3-ethylthiotetradecyl)imidazole and the antimicrobial acid addition salts thereof.

16. A compound of the formula

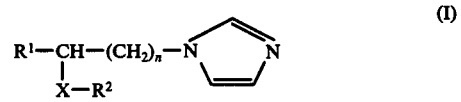

(I)

wherein X is oxygen, n is 1 or 2, and $R^1$ and $R^2$ are each independently straight chain alkyl of from 1 to 12 carbon atoms such that the total number of carbon atoms in $R^1$ and $R^2$ is between 8 and 20; and the antimicrobial acid addition salts thereof.

17. The compound of claim 16 which is 1-(2-nonyloxyoctyl)imidazole and the antimicrobial acid addition salts thereof.

18. The compound of claim 16 which is 1-(2-decyloxyoctyl)imidazole and the antimicrobial acid addition salts thereof.

19. The compound of claim 16 which is 1-(2-octyloxydecyl)imidazole and the antimicrobial acid addition salts thereof.

20. The compound of claim 16 which is 1-(2-hexyloxydodecyl)imidazole and the antimicrobial acid addition salts thereof.

21. The compound of claim 16 which is 1-(2-butoxytetradecyl)imidazole and the antimicrobial acid addition salts thereof.

22. The compound of claim 16 which is 1-(3-decyloxyoctyl)imidazole and the antimicrobial acid addition salts thereof.

23. The compound of claim 16 which is 1-(3-decyloxynonyl)imidazole and the antimicrobial acid addition salts thereof.

24. The compound of claim 16 which is 1-(3-octyloxydecyl)imidazole and the antimicrobial acid addition salts thereof.

25. The compound of claim 16 which is 1-(3-heptyloxyundecyl)imidazole and the antimicrobial acid addition salts thereof.

26. The compound of claim 16 which is 1-(3-hexyloxydodecyl)imidazole and the antimicrobial acid addition salts thereof.

27. The compound of claim 16 which is 1-(3-butoxytetradecyl)imidazole and the antimicrobial acid addition salts thereof.

28. A composition useful for inhibiting the growth of fungi, bacteria or protozoa which comprises an effective amount of a compound of the formula

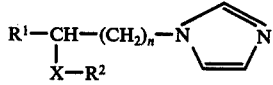 (I)

wherein X is sulfur or oxygen, $n$ is 1 or 2, and $R^1$ and $R^2$ are each independently straight chain alkyl of from 1 to 12 carbon atoms, such that the total number of carbon atoms in $R^1$ and $R^2$ is between 7 and 18 when X is sulfur and between 8 and 20 when X is oxygen; or an antimicrobial acid addition salt thereof; in an admixture with a suitable carrier.

29. The composition of claim 28 suitable for pharmaceutical use wherein the carrier is a pharmaceutically acceptable, non-toxic carrier.

30. The composition of claim 29 for topical administration wherein the compound of Formula (I) is present as between about 0.1 and 10.0 weight percent of the composition.

31. A method of inhibiting the growth of fungi, bacteria or protozoa which comprises applying to a host object containing, or subject to attack by, fungi, bacteria or protozoa, an effective amount of a compound of the formula

 (I)

wherein $R^1$ and $R^2$ are each independently alkyl of from 1 to 12 carbon atoms, cyclohexyl substituted with from one to three lower alkyl groups each having from 1 to 4 carbon atoms, or a group of the formula

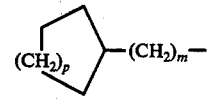

wherein $m$ is an integer of from 0 to 3 and $p$ is an integer of from 1 to 3; X is sulfur or oxygen; $n$ is an integer of from 1 to 8; or an antimicrobial acid addition salt thereof; or a composition containing same as an active ingredient.

32. The method of claim 31 wherein the compound of Formula (I) is administered topically.

33. The method of claim 31 wherein the compound of Formula (I) is administered, orally or parenterally.

* * * * *